United States Patent
Bucher et al.

(10) Patent No.: US 9,459,268 B2
(45) Date of Patent: Oct. 4, 2016

(54) TUBE ROTATOR

(71) Applicants: Marco Bucher, Hohenrain (CH); David Huber, Ebikon (CH)

(72) Inventors: Marco Bucher, Hohenrain (CH); David Huber, Ebikon (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 46 days.

(21) Appl. No.: 14/468,759

(22) Filed: Aug. 26, 2014

(65) Prior Publication Data

US 2015/0079684 A1   Mar. 19, 2015

(30) Foreign Application Priority Data

Aug. 27, 2013 (EP) ..................................... 13181920

(51) Int. Cl.
*G01N 35/02* (2006.01)
*G01N 35/00* (2006.01)
*B01L 9/06* (2006.01)
*G06K 7/10* (2006.01)
*G01N 35/04* (2006.01)

(52) U.S. Cl.
CPC ........... *G01N 35/00732* (2013.01); *B01L 9/06* (2013.01); *G01N 35/0099* (2013.01); *G01N 35/026* (2013.01); *B01L 2200/025* (2013.01); *G01N 2035/00772* (2013.01); *G01N 2035/0413* (2013.01); *G06K 7/10861* (2013.01); *Y10T 436/113332* (2015.01)

(58) Field of Classification Search
CPC ..................................................... G01N 35/02
USPC ....................................... 422/65, 67; 436/47
See application file for complete search history.

(56) References Cited

U.S. PATENT DOCUMENTS

| | | | | |
|---|---|---|---|---|
| 3,898,433 | A | * 8/1975 | Sallet | .................... B07C 5/3412 |
| | | | | 235/435 |
| 3,909,203 | A | * 9/1975 | Young | ................ G01N 35/1083 |
| | | | | 422/67 |
| 4,518,264 | A | * 5/1985 | Nohso | ................ B01F 11/0037 |
| | | | | 366/208 |
| 5,688,361 | A | * 11/1997 | Itoh | ....................... B01L 3/5453 |
| | | | | 156/352 |
| 6,081,326 | A | 6/2000 | Rousseau et al. | |
| 2005/0196323 | A1 | * 9/2005 | Itoh | .................. G01N 35/00732 |
| | | | | 422/82.05 |
| 2005/0252973 | A1 | 11/2005 | Itoh | |
| 2006/0037709 | A1 | * 2/2006 | Itoh | .......................... B65C 9/32 |
| | | | | 156/446 |

FOREIGN PATENT DOCUMENTS

| | | |
|---|---|---|
| EP | 0 972 744 A2 | 1/2000 |
| WO | 2006/057768 A2 | 6/2006 |
| WO | 2013/108169 A1 | 7/2013 |

* cited by examiner

*Primary Examiner* — Arlen Soderquist
(74) *Attorney, Agent, or Firm* — Dinsmore & Shohl LLP

(57) ABSTRACT

A tube rotator for rotating test tubes arranged in a tube rack as well as a system and process for reading information of machine-readable labels of the test tubes are disclosed. The tube rotator may comprise a pivoted lever having two lever arms, a friction wheel rotatably fixed to one lever arm and arranged to be brought in or out of contact with at least one test tube for rotating the test tube by friction. A first actuator may be rotatably coupled to the friction wheel, and a pretensioner which is capable of generating a pretensioning force may act on the lever for pivoting the lever in one pivoting direction. An eccentric may be rotatably fixed with respect to the base and arranged to roll off the other lever arm for pivoting the lever in another pivoting direction. A second actuator may be rotatably coupled to the eccentric.

15 Claims, 4 Drawing Sheets

TUBE ROTATOR

TECHNICAL FIELD

The present disclosure is in the field of biochemical research, biochemical routine analytics, clinical diagnostics and clinical research, and relates to a tube rotator for rotating test tubes in a tube rack for reading machine-readable information provided by labels attached to the test tubes.

BACKGROUND

In recent years, automated analytical instruments offering a variety of analytical methods have become commercially available. Modern analytical instruments usually are adapted to process samples contained in standard sample vessels such as test tubes. In order to process many samples in a batch-wise or continuous manner, it is known to arrange plural test tubes in dedicated tube holders usually referred to as "tube racks". In order to identify samples and allocate test results to specific samples, it is convenient to attach labels to the test tubes providing machine-readable information with respect to the samples contained.

Modern analytical instruments usually come with stationary readers for reading the information provided by the labels of test tubes. Consequently, the labels of the test tubes are to be brought in an appropriate reading position with respect to the reader so that the information can be retrieved. However, due to the fact that test tubes usually are held in a loose-fit manner in the tube rack, the test tubes may be subject to inadvertent rotational movements, especially when the tube rack is handled, e.g., for transport purposes, so that the angular position of the test tubes may be undefined. Accordingly, when it comes to reading of the sample information, the labels may not be readable so that the information cannot be retrieved. It, therefore, may be required to rotate the test tubes to make the labels readable.

It is known to use test tube grippers for the automated rotation of test tubes. Grippers, however, are rather cost-expensive and require much constructional space which is detrimental to the down-sizing of instruments. Furthermore, grippers are complicated in construction and require a highly sophisticated control to achieve sufficient process safety. Moreover, the use of grippers may cause an increased wear of the test tubes.

U.S. Pat. No. 6,081,326 discloses a device, capable of coming laterally in contact with a test tube contained in a tube rack, for rotating the test tube by friction.

SUMMARY

In light of the foregoing, the inventors have found that it is desirable to provide an improved apparatus for rotating test tubes arranged in tube racks so as to enable reading of machine-readable information provided by labels attached to the test tubes.

In one of the various embodiments disclosed herein, a tube rotator for rotating test tubes arranged in a tube rack, and which can comprise a pivoted lever having two lever arms pivotably fixed to a base so as to be pivotable around a pivoting axis between the two lever arms is disclosed. A friction wheel can be rotatably fixed to one lever arm and arranged to be brought in or out of contact with at least one test tube for rotating the at least one test tube by friction. A first actuator can be rotatably coupled to the friction wheel for rotating the friction wheel. A pretensioner capable of generating a pretensioning force acting on the pivoted lever for pivoting the pivoted lever in one pivoting direction also can be provided. An eccentric rotatably can be fixed with respect to the base and arranged to roll off the other lever arm for pivoting the pivoted lever in the other pivoting direction. A second actuator rotatably can be coupled to the eccentric for rotating the eccentric.

In another one of the various embodiments disclosed herein, a process for reading information of machine-readable labels of test tubes arranged in a tube rack is disclosed. The process can comprise having the tube rack pass a reader for reading information provided by the labels, bringing a friction wheel fixed to a pivoted lever in contact with at least one test tube by pivoting the pivoted lever, and rotating the friction wheel so as to rotate the test tube by friction. The process can further comprise reading information provided by a machine-readable label of the at least one test tube, and bringing the friction wheel out of contact with the at least one test tube.

Other and further features and advantages of the invention will appear more fully from the following description.

BRIEF DESCRIPTION OF THE DRAWINGS

The accompanying drawings, which are incorporated in and constitute a part of the specification, illustrate some of the various embodiments of the invention, and together with the general description given above and the detailed description given below, serve to explain the principles of the invention.

DETAILED DESCRIPTION

Figure 1:
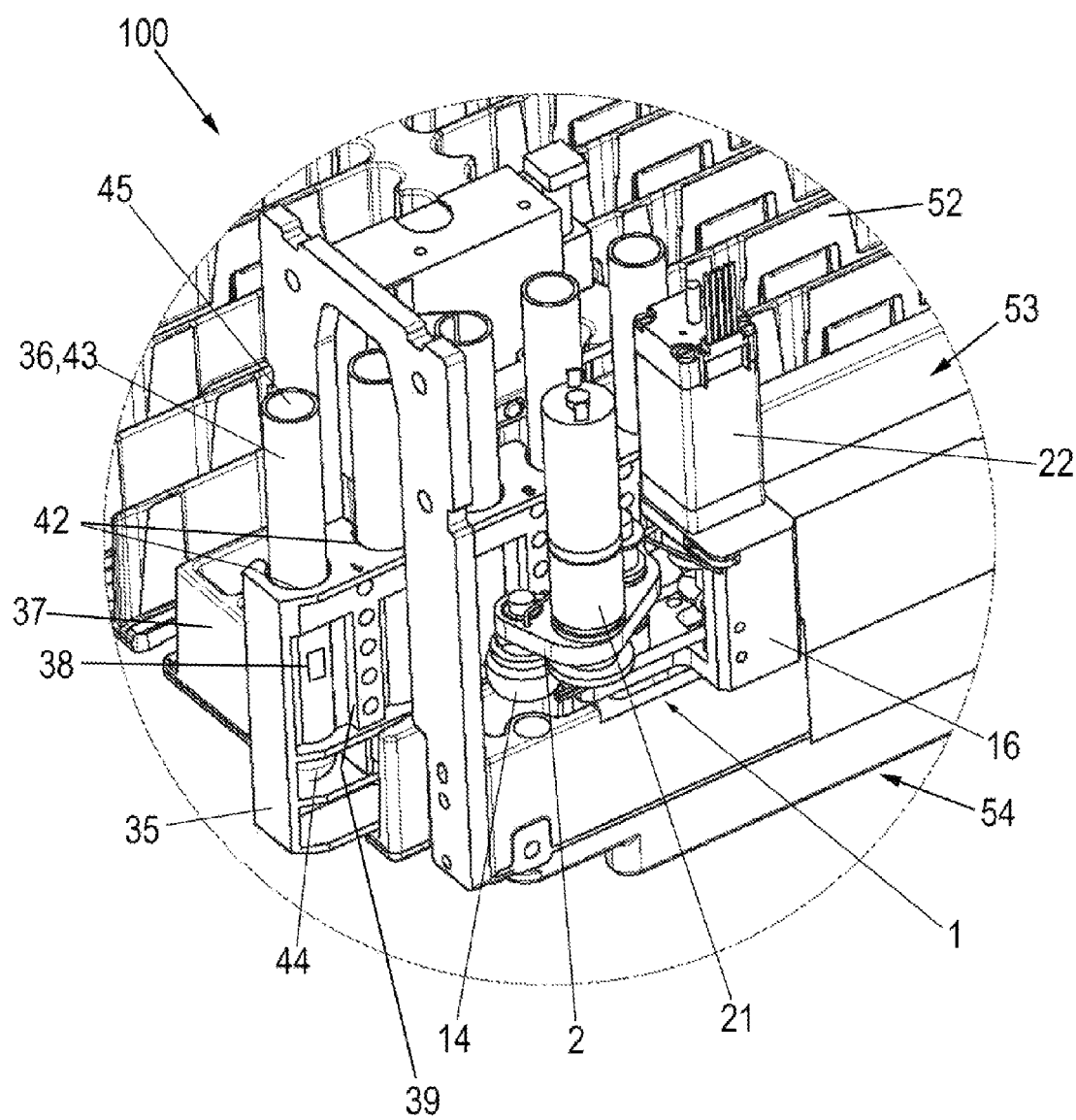
FIG. 1 is a perspective view of a detail of an analytical instrument for analyzing samples illustrating a tube rotator for rotating test tubes according to an embodiment of the invention.

A "sample tube", herein interchangeably referred to as a "tube", is either a sample collection test tube, also called "primary tube", used to receive a sample from a patient and to transport the sample contained therein to an analytical laboratory for diagnostics purposes, or a "secondary tube", which may be used to receive an aliquot of sample from a primary tube. A primary sample tube is typically made of glass or plastics, has a closed end and an open end, typically closed by a closure. The closure may be of different materials and may assume different shapes and colors, typically associated with the type of tube, i.e. the type of sample therein or the type of conditions the sample therein is subjected to or the type of process the tube and sample therein is going to be subjected to. A secondary tube is typically made of plastics and may have a lower degree of variation of size and type with respect to primary tubes. In particular, secondary tubes may be smaller than primary tubes and be designed to be closed with one type or similar types of closure, e.g. of the screw type. The test tube can, e.g., be a tubular test tube which may, e.g., have a cylindrical shaft closed on the bottom side by a rounded, e.g. hemispherical, bottom. The tubular test tube has a generally round profile as sectioned perpendicular to the shaft axis.

A "machine-readable label", herein interchangeably referred to as a "label", provides information, in particular coded information (code) which can be retrieved to identify and, optionally, specify a sample contained in the test tube. Coded information can, e.g., be stored as a barcode, two-dimensional code or an alphanumerical code. Labels can be attached to test tubes, e.g., to the cylindrical walls of tubular test tubes. As used herein, a label can also be an electronic tag for electronically storing and retrieving information, e.g. a RFID-tag.

A "tube rack", herein interchangeably referred to as a "rack", relates to a tube holder provided with a plurality of seats for holding test tubes. Test tubes arranged on the rack may have a loose fit so as to be subject to rotational movements in controlled or uncontrolled manner. The tube rack can, e.g., be configured to hold test tubes in an upright manner.

A "tube reader", herein interchangeably referred to as a "reader", relates to a device for retrieving machine-readable information provided by a label. Specifically, the reader can, e.g., be capable of reading coded information such as barcodes. The reader can be, e.g., configured to opto-electronically read information provided by a label.

According to a first aspect of the invention, a new apparatus for rotating test tubes arranged in a tube rack, in the following denoted as a "tube rotator", for changing the angular position of the test tubes is disclosed herein.

In one embodiment, the apparatus can comprise a pivoted lever having two lever arms, with the pivoted lever being pivotably fixed to a stationary base so as to be pivotable around a pivoting axis located between the two lever arms. Accordingly, the lever can be pivoted in two opposing pivoting directions, also referred to as a "first pivoting direction" and a "second pivoting direction". In one preferred embodiment, the lever axis has a vertical orientation so that the lever can be pivoted in a horizontal plane.

In one embodiment, the apparatus can comprise a driven friction wheel for rotating test tubes by friction which is rotatably fixed to the first lever arm and arranged to be brought in or out of contact with at least one test tube by pivoting the lever. The friction wheel is for rotating (i.e. changing the angular position of) the test tube by friction. Specifically, the friction wheel can be brought in or out of contact with the cylindrical shaft of at least one tubular test tube. In one embodiment, adapted to a vertical orientation of test tubes in the tube rack, the friction wheel can have a vertical wheel axis and thus can be rotated in a horizontal plane.

In one embodiment, the apparatus can comprise a first actuator, coupled to the friction wheel for rotation. The first actuator can be, e.g., configured as an electric motor, provided with a driven shaft rotatably coupled to the friction wheel. In one embodiment, the first actuator can be a DC-motor (DC=direct current). Accordingly, the friction wheel can be actively rotated so as to passively rotate at least one test tube by friction.

In one embodiment, the first actuator can be fixed to the pivoted lever and, thus, can be moved together with the lever. Such construction is particularly compact and therefore advantageous for reducing the overall constructional space of the apparatus. Furthermore, the friction wheel can be easily coupled for rotation to the first actuator.

In one embodiment, the apparatus can comprise a pretensioner, capable of generating a pretensioning force acting on the lever for pretensioning the pivoted lever in one pivoting direction. In one embodiment, the pretensioner can be configured as a leg spring provided with two legs, capable of generating an elastic force by moving one leg with respect to the other leg, wherein one leg is fixed to one lever arm and the other leg is fixed with respect to the base. This embodiment enables an easy and cost-efficient production of the apparatus.

In one embodiment, the apparatus can comprise a rotatable eccentric arranged to roll off the second lever arm for pivoting the lever in the pivoting direction counteracting the pretensioning force of the pretensioner.

In one embodiment, the apparatus can comprise a second actuator coupled to the eccentric in a manner to rotate the eccentric. In one embodiment, the second actuator can be configured as an electric motor, e.g., as a step motor, capable of rotating the eccentric in a step-wise manner. In one embodiment, the eccentric can comprise a disk eccentrically fixed to a driven shaft of the second actuator for rotating the eccentric.

Accordingly, the friction wheel can be readily brought in or out of contact with at least one test tube by rotating the lever. In one embodiment, the friction wheel can be brought in contact with at least one test tube by rotating the lever in the first pivoting direction caused by the pretensioning force and out of contact by rotating the lever in the second pivoting direction caused by the eccentric rolling off the second lever arm. In an alternative embodiment, the friction wheel can be brought in contact with at least one test tube by rotating the pivoted lever in the first pivoting direction caused by the eccentric rolling off the second lever arm and out of contact by rotating the lever in the second pivoting direction caused by the pretensioning force.

Specifically, in one embodiment, an apparatus for rotating test tubes arranged in a tube rack can comprise a pivoted lever having two lever arms, pivotably fixed to a base so as to be pivotable around a pivoting axis between the two lever arms. A friction wheel, for rotating the test tubes by friction, can be rotatably fixed to the first lever arm and arranged to be brought in or out of contact with at least one test tube by pivoting the lever for rotating the test tube. A first actuator can be rotatably coupled to the friction wheel for rotating the friction wheel. A pretensioner can be provided which is capable of generating a pretensioning force that acts on the lever for pivoting the lever in one pivoting direction. A rotatable eccentric can be arranged to roll off the second lever arm for pivoting the lever in the other pivoting direction, and a second actuator can be rotatably coupled to the eccentric for rotating the eccentric.

As a result, an apparatus according to any one of the various embodiments of the invention enables a simple, compact and cost-effective rotation of at least one test tube arranged in a tube rack in order to make machine-readable information provided by a label attached to the test tube readable by a stationary label reader. One of the noted major advantage, and not limited thereto, is given by the fact that the test tubes can be rotated without any tilting action imposed on the test tubes. Accordingly, the test tubes can maintain, e.g., an upright orientation facilitating further processing of samples.

In one embodiment, the apparatus can comprise a light barrier comprising a light path between a light source and a light detector, which is capable of indicating an interrupted or a not interrupted condition of the light path. Furthermore, a light-shading element, capable of interrupting the light path, can be fixed with respect to the eccentric so as to be rotatable together with the eccentric. Specifically, the light-shading element can be configured in such a manner that the condition of the light path is changed depending on whether the friction wheel is brought in or out of contact with the test tube. Accordingly, it can be reliably determined whether the friction wheel is in or out of contact with a test tube in order to improve the process safety of the apparatus. The light-shading element can, e.g., comprise a segment of a circular disk. Combined with the step motor for driving the eccentric, the apparatus provides an easy and cost-effective way of bringing the friction wheel in or out of contact with a test tube and controlling the outcome. Specifically, it is not required to use two DC-electric motors combined with a decoder to perform this task which involve much higher costs.

According to a second aspect of the invention, a new system for reading information of machine-readable labels of test tubes is disclosed herein.

In one embodiment, the system can comprise a tube rack for holding test tubes, one or more test tubes arranged in the tube rack provided with labels for storing machine-readable information, a reader, capable of reading information provided by the labels, and a tube rack transport mechanism, capable of transporting the tube rack with respect to the reader. The tube rack transport mechanism can have the tube rack pass the reader and transport the tube racks in a reading position in which the reader can read the machine-readable information of the label of at least one test tube contained in the tube rack. The system further can comprise a rotator for rotating test tubes according to one or more of the above-described embodiments.

In one embodiment, the system can comprise a controller, configured to control a transport mechanism to have a tube rack pass the reader, a rotator to rotate at least one test tube, and a reader to read information provided by labels of the test tubes. Consequently, information provided by the labels of the test tubes can be reliably read by the reader in order to identify and/or specify samples contained in the test tubes. Accordingly, test results can be allocated to specific samples.

In one embodiment, the controller can be configured to control the rotator in a manner that a friction wheel is brought in contact with a test tube only if the information provided by the label of the test tube is not readable. Accordingly, the system can advantageously save time and costs to process samples.

In one embodiment, the controller can be configured to control a transport mechanism in a manner that transport of a tube rack is not stopped if a label of a test tube is readable. Accordingly, the system can advantageously save time and costs to process samples.

In one embodiment, the controller can be configured to control rotation of a first actuator in a manner that a friction wheel is rotated only if it is indicated by a light-barrier that the friction wheel is in contact with a test tube. Accordingly, the system can advantageously save time to process samples.

In one embodiment, the controller can be configured to control a transport mechanism in a manner that a tube rack is kept stationary with respect to a reader until it is indicated by a light barrier that a friction wheel is out of contact with a test tube. Accordingly, movement of the tube rack is prevented until the friction wheel is out of contact with the test tube so as to avoid mechanical damage or improper handling of the tube rack and/or test tubes.

According to a third aspect of the invention, a new process for reading information of machine-readable labels of the test tubes arranged in a tube rack is disclosed herein.

The process comprises the following steps of:

having the tube rack pass a reader for reading information provided by labels of test tubes arranged in the tube rack;

bringing a friction wheel fixed to a pivoted lever in contact with at least one test tube by pivoting the lever;

rotating the friction wheel so as to rotate the test tube by friction;

reading information provided by the label of the test tube; and bringing the friction wheel out of contact with the test tube.

In one embodiment, the friction wheel is brought in contact with a test tube only if the information provided by the label of the test tube is not readable. In one embodiment, the transport of a tube rack is interrupted only if the machine-readable label of a test tube is not readable. In one embodiment, the friction wheel is rotated only if it is indicated that the friction wheel is in contact with a test tube. In one embodiment, the tube rack is kept stationary with respect to the reader until it is indicated that the friction wheel is out of contact with a test tube.

The above-described embodiments of the various aspects of the invention may be used alone or in any combination thereof without departing from the scope of the invention. Further various embodiments of the present invention will be described in detail below with reference to the accompanying drawings, where like designations denote like or similar elements.

As illustrated in FIG. 1, a tube rotator 1 for rotating test tubes is disclosed. The tube rotator 1 can be part of a system for processing samples, generally referred to at reference numeral 100, such as an analytical instrument for processing samples by one or more analytical methods. The system 100 can comprise a mount 52 for arranging various components and mechanisms for processing samples. Specifically, the system 100 can comprise a rack transport mechanism 53 (not further detailed) for transporting a tube rack 35, e.g., with respect to a stationary reader 37. Stated more particularly, the rack transport mechanism 53 can be operated to have the tube rack 35 pass the reader 37 for reading labels 38 providing machine-readable information attached to test tubes 36 received in a tube rack 35. In FIG. 1, one tube rack 35 is shown for the purpose of illustration only.

Figure 2A:
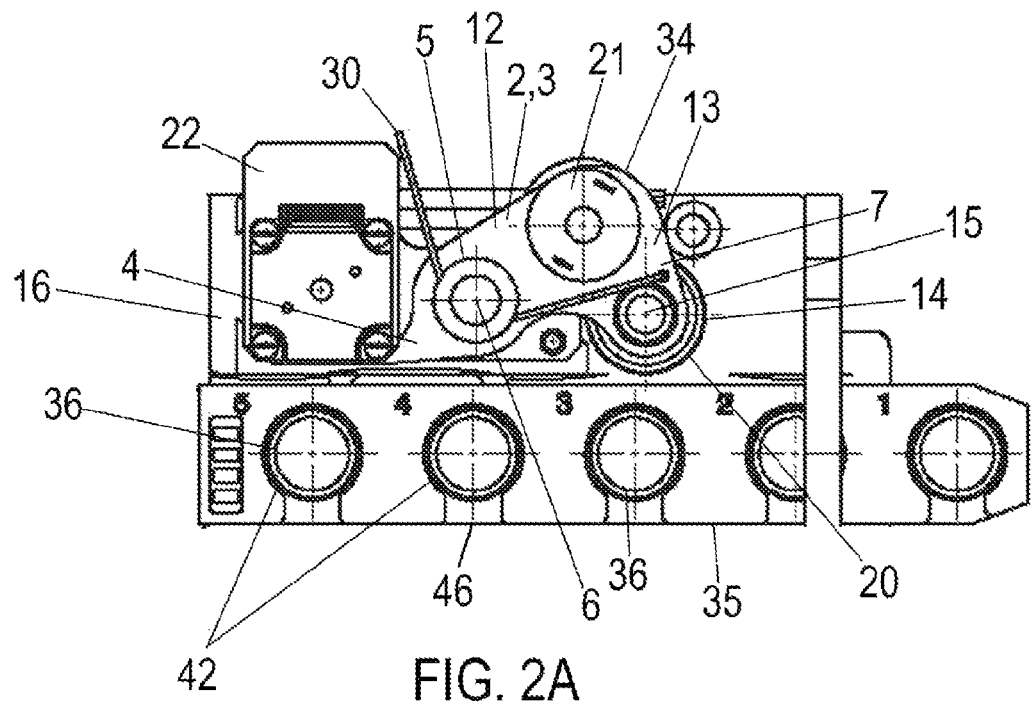
FIGS. 2A-2B are top views of the tube rotator of FIG. 1, with the friction wheel being out of contact with a test tube (FIG. 1A) or in contact with a test tube (FIG. 1B)
Figure 2B:
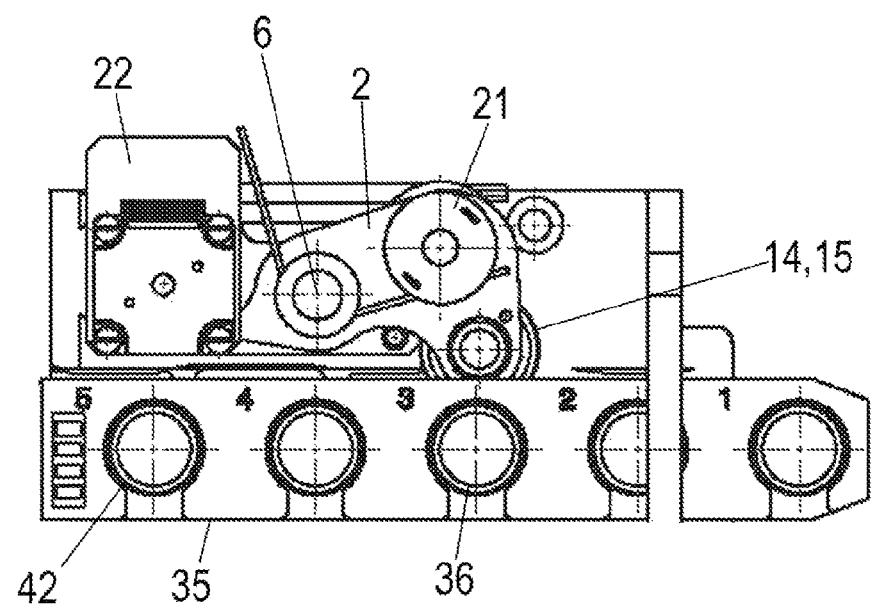

With particular reference to FIGS. 1, 2A and 2B, the tube rack 35 comprises plural tube seats 42, each of which having a substantially circular cross section, adapted to receive one tubular test tube 36 in a loose-fit manner and in an upright position. As illustrated, the tube rack 35 contains a number of, e.g., five tube seats 42 arranged side-by-side in a row. Those of skill in the art will appreciate that any other number of tube seats 42 can be envisaged according to the specific demands of the user. On the facing side of the tube rotator 1, each tube seat 42 is provided with a rectangular window 39 enabling a friction wheel 14 of the tube rotator 1 to have contact with the test tube 36 contained in the tube seat 42 so as to rotate the test tube 36 by friction. On the facing side of the reader 54, each tube seat 42 has a longitudinal gap 46 enabling the reader 54 to read information provided by the label 38 attached to the test tube 36 arranged in the tube seat 42. As illustrated, each of the tubular test tubes 36 has a cylindrical tube shaft 43 and a rounded, e.g. hemispherical, tube bottom 44 so as to have a generally circular profile as sectioned through the tube shaft 43. Due to being arranged with a loose fit, each of the test tubes 36 can be rotated in the tube seat 42 around the shaft axis 45 so as to change the angular position of the test tube 36.

Figure 3:
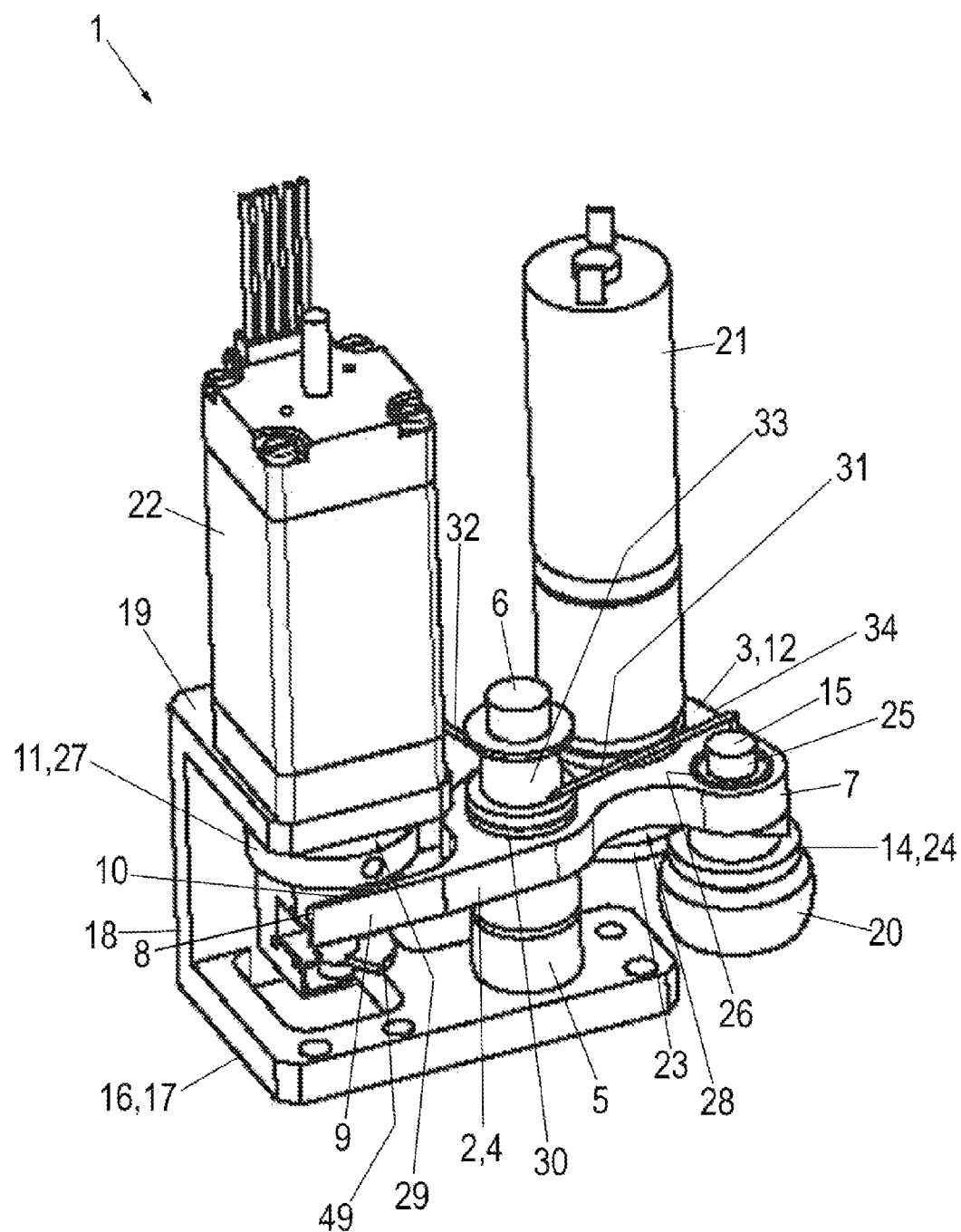
FIG. 3 is a perspective front view of the tube rotator of FIG. 1.

In the following, with particular reference to FIGS. 2A, 2B and 3, the tube rotator 1 is explained in detail. The tube rotator 1 comprises a stationary base 16 having a generally U-shaped profile formed by a plate-like bottom portion 17 for fixing the tube rotator 1 at the bottom side, a plate-like top portion 19 in parallel alignment to the bottom portion 17 and a plate-like rear portion 18 connecting the bottom and top portions 17, 19. The tube rotator 1 further includes a pivoted lever 2 configured as a horizontally aligned plate having a first lever arm 3 and a second lever arm 4. The pivoted lever 2 is pivotably fixed to a vertical pillar 5, with the pillar 5 being fixed to the bottom portion 17. Consequently, the pivoted lever 2 can be pivoted around a vertical lever axis 6 between the two lever arms 3, 4 as given by a central symmetry axis of the pillar 5. As a result, the lever 2 can be pivoted in two pivoting directions, i.e. a first pivoting direction (clockwise as seen from above) and a second pivoting direction (counter-clockwise as seen from above). The first lever arm 3 comprises a first lever portion 12 and a second lever portion 13, with the first lever portion 12 being directly connected to the second lever arm 4. As can best be seen in FIGS. 2A and 2B, the first lever arm 3 has an angled outer contour 34, with an angle of 90° being formed between the first and second lever portions 12, 13.

The first lever arm 3 comprises a first end portion 7 provided with the friction wheel 14. The friction wheel 14 is rotatably fixed to the first lever arm 3 so as to be rotatable in a horizontal plane around a vertical wheel axis 15. A vertical swivel pin 25 of the friction wheel 14 is rotatably coupled to a swivel gear 26 of the first end portion 7 for rotatably fixing the friction wheel 14 to the first lever arm 3, with the lever axis 6 being in parallel alignment to the wheel axis 15 as given by a central axis of the swivel pin 25. The friction wheel 14 is provided with a rubber ring 20 which can be brought in frictional contact with a test tube 36. The second lever arm 4 tapers from the lever axis 6 towards a second end portion 8, e.g., configured as a narrowing tongue 9. On one side, the tongue 9 has a contact face 10 for contacting an eccentric 11.

The tube rotator 1 further comprises a first (DC) electric motor 21 (not configured as a step motor) for driving the friction wheel 14. Specifically, the first electric motor 21 is fixed to the first lever arm 3 in a middle position of the first and second lever portions 12, 13. Consequently, the first electric motor 21 can be moved together with the lever 2. A driven first shaft 28 of the first electric motor 21 penetrates the first lever arm 3 so as to be arranged at the lower side of the first lever arm 3. A first gearwheel 23 is fixed to the first shaft 28 and in meshing engagement with a second gearwheel 24 fixed to the swivel pin 25 for coupling the first electric motor 21 to the friction wheel 14. Consequently, by driving the first shaft 28, the friction wheel 14 can be driven via the meshing gearwheels 23, 24.

The tube rotator 1 further comprises a leg spring 30 comprising a first leg 31 and a second leg 32 for pretensioning the lever 2 in one pivoting direction. The leg spring 30 is wound around a pin 33 protruding from the base-fixed, vertical pillar 5 having the first leg 31 fixed to the first end portion 7 of the first lever arm 3 and the second leg 32 clamped against a second electric motor 22 in a pretensioned state in which the elastic force pivots the lever 2 in the first pivoting direction.

The second electric motor 22 is configured as a step motor for driving an eccentric 11. Specifically, the second electric motor 22 is fixed to the top portion 19 of the base 16 so as to be stationary with respect to the lever 2. A driven second shaft 29 of the second electric motor 22 penetrates the top portion 19 so as to be arranged at the lower side of the top portion 19. As can best be seen in FIGS. 4A and 4B, the eccentric 11 is embodied as a disk 27 fixed to the second shaft 29 in an eccentric manner resulting in a more protruding first disk portion 50 and a less protruding second disk portion 51 relative to the second shaft 29. The disk 27 is arranged to be in permanent contact with and roll off the contact face 10 of the tongue 9 when the disk 27 is rotated.

Figure 4A:
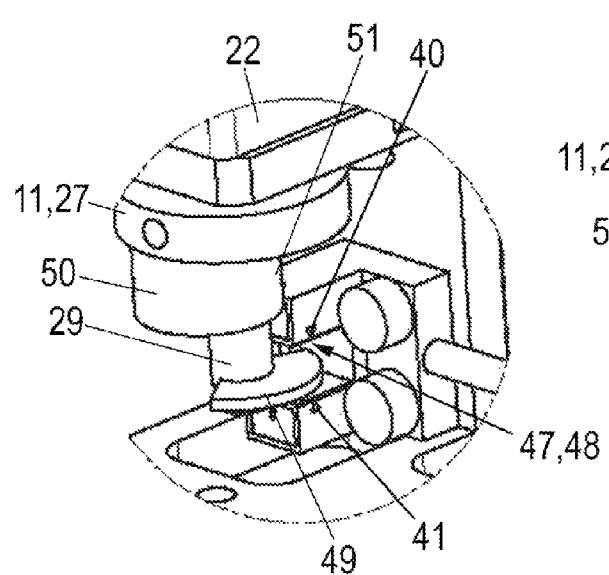
FIG. 4A-4B are perspective side views of the tube rotator of FIG. 1, with the eccentric in a first rotating position (FIG. 4A) or a second rotating position (FIG. 4B).
Figure 4B:
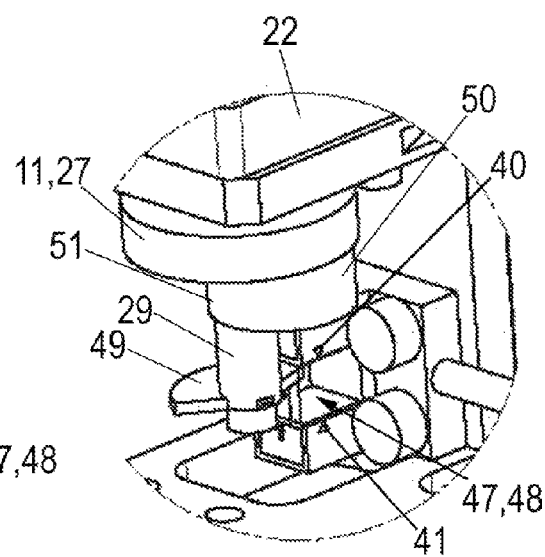

With particular reference to FIGS. 4A and 4B, the tube rotator 1 further comprises a light barrier 47 having a light path 48 between a light source 40 and a light sensor 41, capable of indicating an interrupted or non-interrupted condition of the light path 48. Those of skill in the art are aware of the mechanism of light barriers so that it is not necessary to elucidate it further herein. The light barrier 47 further comprises a light-shading element 49 configured as a segment of a circular disk.

Specifically, the light-shading element 49 is fixed to the second shaft 29 and thus can be rotated together with the disk 27 of the eccentric 11. Consequently, the light barrier 47 can be used to reliably detect the angular position of the eccentric 11 so as to determine whether the friction wheel 14 is in or out of contact with a test tube 36. Stated more particularly, as illustrated in FIG. 4A, if the broader first disk portion 50 faces the contact face 10 meaning that the friction wheel 14 is out of contact with a test tube 36, the light-shading element 49 is outside the light path 48, and, as illustrated in FIG. 4B, if the smaller second disk portion 51 faces the contact face 10 meaning that the friction wheel 14 is in contact with a test tube 36, the light-shading element 49 interrupts the light path 48. Accordingly, contact between the friction wheel 14 and a test tube 36 can readily be detected via the light barrier 47. It goes without saying that the non-contacted state of the friction wheel 14 can alternatively be detected by interrupting the light path 48.

When it comes to reading of the information of a label 38, a test tube 36 must be brought in an appropriate position, in the following denoted as a "reading position", in front of the reader 37 and have an angular position with respect to the reader 37 enabling retrieving of the stored information. In reading position, the gap 46 of the tube seat 42 faces the reader 37 enabling reading of the label 38. Simultaneously, the friction wheel 14 can access the test tube 36 through the window 39 of the tube seat 42 for rotating a test tube 36 in reading position if the label 38 is not readable.

Stated more particularly, the rack transport mechanism 53 is operated to transport a tube rack 35 along the reader 37 so that test tubes 36 arranged in the tube rack 35 successively pass the reader 37. In an embodiment, the transport of the tube rack 35 is interrupted if a test tube 36 is in reading position, irrespective of the fact whether its label 38 is readable or not. The stop period can be reduced if the friction wheel is not brought in contact with the test tube 36 in case the label is readable.

In an alternative embodiment, the tube rack 35 is transported without interruption if the label 38 of a test tube 36 in reading position is readable and interrupted only if the label 38 is not readable. If the label 38 is not readable, the tube rotator 1 is operated to rotate the test tube 36 in reading position. Starting from a position illustrated in FIG. 2A, by bringing the smaller second disk portion 51 in a position to face the contact face 10, the elastic force of the leg spring 30 rotates the lever 2 in the first pivoting direction and the rubber ring 20 is pushed against a test tube 36 so as to reach a position as illustrated in FIG. 2B in which the friction wheel 14 is in contact with the test tube 36. By driving the friction wheel 14 using the first electric motor 21, the test tube 36 can be rotated by friction in order to make the machine-readable information of the label 38 readable. The friction wheel 14 can, e.g., continuously be driven to perform at least a full turn of the test tube 36 wherein the information provided by the label 38 can be read while rotating the test tube 36.

Alternatively, the test tube 36 can be rotated for less than a full turn until the information provided by the label 38 can be read, e.g., by having a facing position with respect to the reader 37. The first electric motor 21 can, e.g., be coupled to a positioning sensor (encoder), capable of determining the angular position of the friction wheel 14 and verifying rotation of the friction wheel 14, or can be actuated in a time-controlled manner. Then, having read the information of the label 38, starting from a position illustrated in FIG. 2B, by bringing the broader first disk portion 50 in a position to face the contact face 10, the lever 2 is pivoted in the second pivoting direction counteracting the elastic force of the leg spring 30 to reach a position as illustrated in FIG. 2A. The disk 27 is, e.g., rotated by an angle of 180° in order to bring the first disk portion 50 in contact with the contact face 10. Step-wise rotation of the eccentric 11 can readily be reached by the second electric motor 22 configured as a step motor. Accordingly, the rubber ring 20 is brought out of contact with the test tube 36. The light barrier 47 is used to check if the friction wheel 14 is out of contact with the test tube 36. Then, transport of the tube rack 35 can be continued until another test tube 36 is in reading position, with the transport of the tube rack 35 being stopped only if the label 38 is not readable.

Obviously, many modifications and variations of the embodiments of the present invention are possible in light of the above description. It is therefore to be understood, that within the scope of appended claims, the invention may be practiced otherwise than as specifically devised. For instance, the tube rotator 1 can be configured in a manner that the friction wheel 14 is brought in contact with a test tube 36 by action of the eccentric 11 and out of contact with the test tube 36 by the elastic force of the leg spring 30.

The tube rotator 1 according to any one of the various embodiments of the invention has many advantages over the prior art. One of the noted major advantages, and not limited thereto, is given by the fact that the friction wheel 14 is pushed horizontally against a test tube 36 without having any tilting effect on the tube rack 35 and/or test tube 36. Accordingly, the handling of the tube rack 35 and the safety and reliability of the process can be strongly improved. Furthermore, the friction wheel 14 is pushed against a test tube 36 in a rather homogenous manner resulting from a homogeneous force distribution. Moreover, the contacted or non-contacted state of the friction wheel 14 can readily be determined by use of the light barrier 47 allowing for a robust process control, precise error handling and improved process safety. The transport of the tube rack 35 can be reliably avoided in case the friction wheel 14 is in contact with a test tube 36. Generally, the tube rotator 1 is highly compact in design resulting in a rather small foot-print. Furthermore, the tube rotator 1 is simple and robust in construction so as to be suitable for long-term maintenance-free usage. It comprises only few components enabling low-cost and easy production and small tolerances due to the small number of components. The information of the labels 38 can be read by using only two electric motors, with only one of which being configured as a DC motor so as to save costs. The workflow for processing samples can be made highly-efficient by interrupting the transport of the tube rack only if the label of a test tube in reading position is not readable.

What is claimed is:

1. A tube rotator for rotating test tubes arranged in a tube rack, comprising:
    a pivoted lever having two lever arms pivotably fixed to a base so as to be pivotable around a pivoting axis between the two lever arms;
    a friction wheel rotatably fixed to one lever arm and arranged to be brought in or out of contact with at least one test tube for rotating the at least one test tube by friction;
    a first actuator rotatably coupled to the friction wheel for rotating the friction wheel;
    a pretensioner capable of generating a pretensioning force acting on the pivoted lever for pivoting the pivoted lever in one pivoting direction;
    an eccentric rotatably fixed with respect to the base and arranged to roll off the other lever arm for pivoting the pivoted lever in the other pivoting direction; and
    a second actuator rotatably coupled to the eccentric for rotating the eccentric.

2. The tube rotator according to claim 1, wherein the eccentric comprises a disk, eccentrically fixed to a rotatable shaft of the second actuator.

3. The tube rotator according to claim 1, wherein the pretensioner comprises a leg spring provided with two legs, wherein one leg is fixed to one lever arm and the other leg is fixed with respect to the base.

4. The tube rotator according to claim 1, wherein the pivoting axis of the pivoted lever is vertically oriented so as to rotate the pivoted lever in a horizontal plane.

5. The tube rotator according to claim 1, comprising:
    a light barrier having a light path which is capable of indicating an interrupted or non-interrupted condition of the light path, and
    a light-shading element for interrupting the light path, fixed with respect to the eccentric, wherein the light-shading element is configured in such a manner that the condition of the light path is changed depending on whether the friction wheel is in or out of contact with the at least one test tube.

6. The tube rotator according to claim 5, wherein the light-shading element comprises a segment of a disk.

7. The tube rotator according to claim 1, wherein the first actuator is fixed to the pivoted lever.

8. The tube rotator according to claim 1, wherein the first actuator is a DC-motor and the second actuator is a step motor.

9. A system for reading information of machine-readable labels of test tubes, comprising:
    a tube rack for holding test tubes;
    one or more test tubes arranged in the tube rack, with the test tubes carrying labels for providing machine-readable information;
    a reader capable of reading information provided by the labels;
    a rack transport mechanism capable of transporting the tube rack;
    a tube rotator for rotating at least one test tube according to claim 1; and
    a controller configured to control:
        the rack transport mechanism to have the tube rack pass the reader,
        the tube rotator to rotate the at least one test tube, and
        the reader to read information provided by a label of the at least one test tube.

10. The system according to claim 9, wherein the controller is configured to control the tube rotator in a manner that the friction wheel is brought in contact with the at least one test tube for rotating the at least one test tube only if the information provided by the label of the test tube is not readable.

11. The system according to claim 9, wherein the controller is configured to control the rack transport mechanism in a manner that the transport of the tube rack is interrupted only if the label of the at least one test tube is not readable.

12. A process for reading information of machine-readable labels of test tubes arranged in a tube rack, comprising:

having the tube rack pass a reader for reading information provided by the labels;

bringing a friction wheel fixed to a pivoted lever in contact with at least one test tube by pivoting the pivoted lever;

rotating the friction wheel so as to rotate the test tube by friction;

reading information provided by a machine-readable label of the at least one test tube; and bringing the friction wheel out of contact with the at least one test tube, wherein the friction wheel is brought in contact with the at least one test tube only if the information provided by the machine-readable label of the at least one test tube is not readable.

13. The process according to claim 12, wherein the transport of the tube rack is interrupted only if the machine-readable label of the at least one test tube is not readable.

14. The process according to claim 12, wherein the friction wheel is rotated only if it is indicated that the friction wheel is in contact with the at least one test tube.

15. The process according to claim 12, wherein the tube rack is kept stationary with respect to the reader until it is indicated that the friction wheel is out of contact with the at least one test tube.

\* \* \* \* \*